United States Patent
Alfano et al.

(10) Patent No.: US 7,038,208 B2
(45) Date of Patent: May 2, 2006

(54) SYSTEMS AND METHODS FOR NON-DESTRUCTIVELY DETECTING MATERIAL ABNORMALITIES BENEATH A COATED SURFACE

(75) Inventors: Robert R. Alfano, Bronx, NY (US); Iosif Zeylikovich, Brooklyn, NY (US); Wubao Wang, Flushing, NY (US); Jamal Ali, Brooklyn, NY (US); Vincent Benischek, Shrub Oak, NY (US); Yury Budansky, Oakland, NJ (US)

(73) Assignees: The Research Foundation of the City of New York, New York, NY (US); Lockheed Martin Corporation, Bethesda, MD (US)

( * ) Notice: Subject to any disclaimer, the term of this patent is extended or adjusted under 35 U.S.C. 154(b) by 68 days.

(21) Appl. No.: 10/653,473

(22) Filed: Sep. 2, 2003

(65) Prior Publication Data

US 2004/0119018 A1      Jun. 24, 2004

Related U.S. Application Data

(60) Provisional application No. 60/407,475, filed on Aug. 31, 2002.

(51) Int. Cl.
*G01N 21/88* (2006.01)
(52) U.S. Cl. .................................................. 250/341.1
(58) Field of Classification Search ............. 250/341.1, 250/339.11
See application file for complete search history.

(56) References Cited

U.S. PATENT DOCUMENTS

| | | | | |
|---|---|---|---|---|
| 5,962,852 A * | 10/1999 | Knuettel et al. | ....... | 250/339.11 |
| 2001/0047137 A1* | 11/2001 | Moreno et al. | ............. | 600/475 |
| 2002/0093636 A1* | 7/2002 | Komatsuda | .................. | 355/67 |
| 2003/0117620 A1* | 6/2003 | Balas et al. | ................. | 356/326 |
| 2004/0026622 A1 | 2/2004 | DiMarzio et al. | | |
| 2004/0156016 A1* | 8/2004 | Kerr et al. | .................. | 351/206 |

* cited by examiner

*Primary Examiner*—David Porta
*Assistant Examiner*—Marcus Taningco
(74) *Attorney, Agent, or Firm*—Dilworth & Barrese LLP (57) ABSTRACT

The present invention provides systems and methods for non-destructively detecting material abnormalities beneath a coated surface, comprising a mid-infrared (MIR) illumination unit for illuminating an area of the coated surface, and an MIR 2-D imager, which includes an MIR CCD or CMOS camera, for capturing an image of a material abnormalities under the illuminated area of the coated surface. In addition, the system may further comprise a scanning unit for moving the system to a next area.

23 Claims, 8 Drawing Sheets

Imaged with 3-5μm CCD camera

Paint system #1 MIL paint coatings on 3G slide over hairline crack. 10 degree illumination with 1x magnification.

FIG. 8

SYSTEMS AND METHODS FOR NON-DESTRUCTIVELY DETECTING MATERIAL ABNORMALITIES BENEATH A COATED SURFACE

PRIORITY

This application claims priority under 35 U.S.C. § 119 to a provisional application entitled "Cracks and Corrosion Detection Technique" filed in the United States Patent and Trademark Office on Aug. 31, 2002 and assigned Ser. No. 60/407,475, the contents of which are hereby incorporated by reference.

GOVERNMENTAL INFORMATION

This invention is supported in part by: Air Force Office of Scientific Research (AFOSR) under a grant of #F49620-00-1-0378 (RF 47435-00-01); National Science Foundation (NSF) under a grant of #CMS-0135790 (RF 40357-00-01); and NYS TTIP (Technology Transfer Incentive Program) under a grant of #C2000056 (RF 55414-00-01).

BACKGROUND OF THE INVENTION

1. Field of the Invention

The present invention relates generally to systems and methods for non-destructively detecting material abnormalities beneath a surface, and in particular, to systems and methods for detecting corrosion and cracks in metal surfaces beneath a layer of paint using mid-infrared light.

2. Description of the Related Art

Paint or other coatings are typically applied to surfaces to protect the surfaces against corrosion or other damage. In some instances, corrosion, cracking, or other damage (material abnormality) begins under the paint or coating and is undetectable by visual inspection. In addition, the paint itself may crack, while the underlying surface is perfectly fine. This may cause unnecessary repairs. Conventionally, inspections may be carried out by one or more of the following non-destructive imaging (NDI) techniques.

Ultrasonic (pulse echo or through transmission) methods can monitor larger defects of, for example, aircraft structures for a whole field, but are not preferred for detection of early or surface deterioration. The techniques are particularly conducive to rapid imaging of a surface and include magneto-optic eddy current imaging, active thermography, optically aided visual inspection, and spectral imaging.

Magneto-optic imaging (MOI) can image corrosion and cracks over a small area the size of the magneto-optic crystal plate used in a hand-held scanner. However, MOI's sensitivity to top-surface corrosion depends on the degree to which the eddy currents are altered and gives rise to anomalies in the induced magnetic field at the surface. It has not been shown conclusively that the MOI technique can detect incipient corrosion that has not yet produced a significant increase in macroscopic surface roughness.

Active Thermography (AT) is an increasingly important technique for detecting subsurface flaws such as delamination, debonding, and second-surface corrosion. AT has a lower sensitivity to incipient corrosion under paint, however, because (1) the initial stages of corrosion do not significantly increase the thermal impedance of the surface compared to a layer of paint alone, and (2) the detailed resolution of incipient corrosion effects at the top surface requires a very high speed infrared camera to resolve surface transients which may appear only in the few milliseconds after the initial flash lamp illumination. In addition, such equipment is prohibitively expensive for use on a wide scale. However, for significant surface corrosion, AT and MOI have the potential to image significant surface corrosion damage and distinguish it from subsurface effects by employing commercially available instrumentation.

Visual Inspection (VI) is used to determine the extent of corrosion damage on a skin of a surface and around fasteners, for example, after the paint or coating has been stripped. As a nondestructive technique for painted aircraft, visual techniques are not amenable to detection of chemical changes or micro-roughness at the paint/metal interface, unless significant corrosion products penetrate through the thickness of the paint.

Spectral Imaging (SI) techniques generally use a compact multi-spectral imaging sensor. This method is based on the partial transparency of many aircraft paints to specific bands of infrared radiation. Using this method, it is possible to detect changes in the chemistry of the metal surface or the primer by analyzing the amplitude of reflected and emitted radiation at specific wavelengths. The layered depth information, i.e., the state of the surface at different depths below the paint, cannot be deduced from a simple SI approach, however.

Photonic techniques offer a potentially rapid, noninvasive and easy approach to detect corrosion and cracks in situ. Art preservationists use Near-IR (NIR) charge-coupled device (CCD) cameras ($\lambda<2$ μm) to view paintings that have underdrawings not visible with the human eye. Novel methods of a second-harmonic generation (SHG) imaging, and spectral polarization optical imaging have been proposed to detect the early stages of corrosion under thin layers of paint using NIR. One such Example of this technique can be found in U.S. Pat. No. 6,495,833, entitled "Sub-surface Imaging Under Paints and Coatings Using Early Light Spectroscopy," which issued to Alfano et al. on Dec. 17, 2002 (hereinafter referred to as "Alfano").

Alfano discloses near-infrared (NIR) optical imaging systems and methods to non-destructively image (NDI) deteriorations or defects in painted metals and artwork beneath painted surfaces. Specfically, back-scattered light is used to determine suitability to monitor corrosion and cracking in metal beneath paints, up to a thickness of about 500 μm. That is, NIR light, which is in the paint transmission zone spanning from 800 nm to 10,000 nm, can be used to assess the quality of metallic structures below the paint level for incipient and advanced stages of corrosion and cracking. NIR light scattered from paint, corrosion, air voids, and metal can be spatially imaged in micrometer sliced subsurface layers. In addition, spectral, temporal, spatial, non-linear optical, and polarization gates are employed to distinguish phantoms in turbid media, such as painted corroded metal and cracked specimens, e.g., painted surfaces from airplanes, submarines, ships, automobiles, bridges, etc.

However, the systems and methods disclosed in Alfano, which utilize NIR optical imaging, also require a gating system in order to create the detected images. This gating system and tends to create a more complex and costly imaging system. In addition, this method is not capable of detecting the early stages of corrosion under surface thick paint with thickness larger than 40 μm.

In patent application Ser. No. 10/455,662, entitled "Systems and Methods for Non-Destructively Detecting Material Abnormalities Beneath a Coated Surface", which was also filed by Alfano et al., (hereinafter referred to as "Alfano II"), systems and methods are disclosed for detecting the early stages of corrosion under surface thick paint with thickness larger than 40 µm. In Alfano II, a mid-infrared (MIR) detection unit illuminates an area of a coated surface and detects light reflected from the illuminated area of the coated surface, and a processing unit for produces an image from optical characteristics received from the MIR detection unit. However, in Alfano II, the processing of the optical characteristics requires extra time and resources, which adds to the complexity and cost associated with those systems and methods.

Therefore, a need exists for an improved system and method for inspecting surfaces through a coating, such as paint. A further need exists for such a system and method, which improves upon existing techniques and does not suffer from the disadvantages as described above.

SUMMARY OF THE INVENTION

It is, therefore, an object of the present invention to provide improved system and method for detecting corrosion and cracks in metal surfaces beneath a layer of paint.

It is another object of the present invention to provide improved system and method for detecting corrosion and cracks in metal surfaces beneath a layer of paint using mid-infrared light.

It is yet another object of the present invention to provide a system and method for detecting corrosion and cracks in metal surfaces beneath a layer of paint with thickness larger than 40 µm.

To achieve the above and other objects, the present invention provides a system for non-destructively detecting material abnormalities beneath a coated surface, comprising a mid-infrared (MIR) illumination unit for illuminating an area of the coated surface; and an MIR optical 2-D imager for imaging the illuminated area of the coated surface.

In addition, the system may further comprise a scanning unit for moving the MIR illumination unit and/or the optical 2-D imager to a next area.

To achieve the above and other objects, the present invention also provides a method for non-destructively detecting material abnormalities beneath a coated surface, comprising the steps of: illuminating an area of the coated surface with an MIR light source; and imaging the illuminated area of the coated surface to produce a 2-D image.

Additionally, the method may further comprise scanning a next area.

BRIEF DESCRIPTION OF THE DRAWINGS

The above and other objects, features, and advantages of the present invention will become more apparent from the following detailed description when taken in conjunction with the accompanying drawings in which.

DETAILED DESCRIPTION OF PREFERRED EMBODIMENTS

Several preferred embodiments of the present invention will now be described in detail herein below with reference to the annexed drawings. In the drawings, the same or similar elements are denoted by the same reference numerals even though they are depicted in different drawings. In the following description, a detailed description of known functions and configurations incorporated herein has been omitted for conciseness.

In order to determine an improved method for imaging a below a coated surface, various test were performed in order to determine optimal conditions and specification for the system and method. More specifically, tests were performed to determine an optimal IR-range for performing the subsurface imaging.

Figure 1:
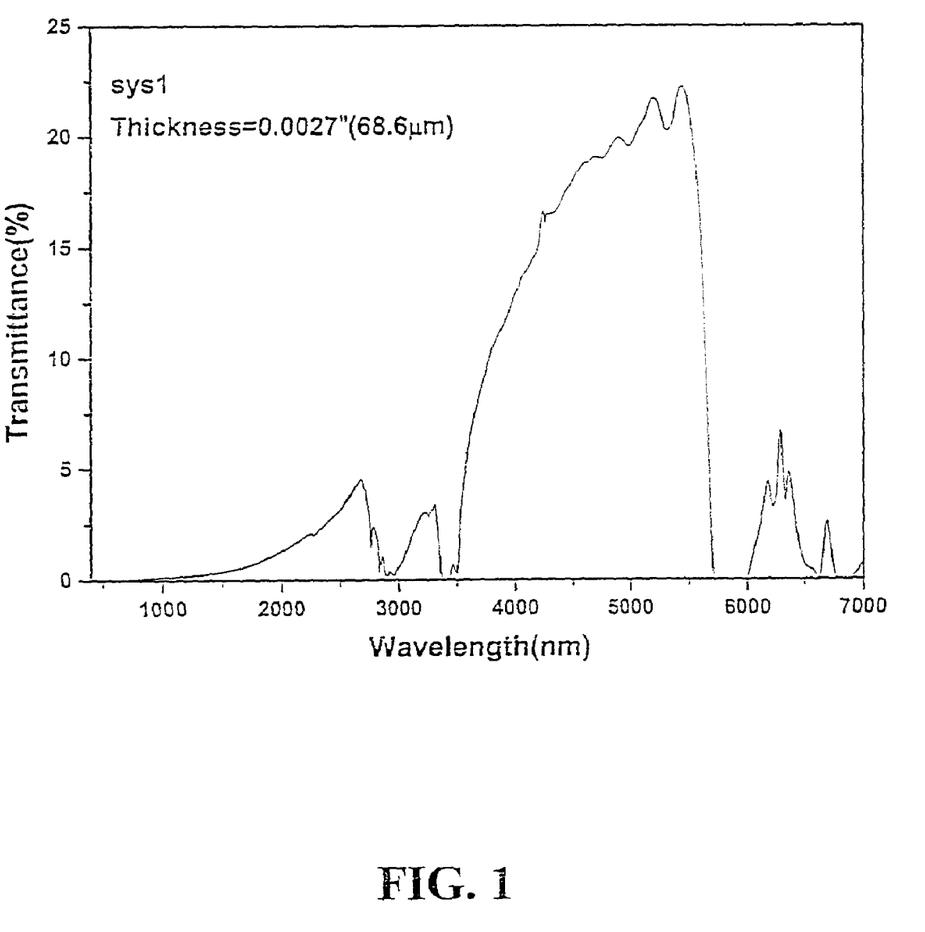
FIG. 1 is a graph illustrating a transmission curve of a paint.

FIG. 1 is a graph illustrating a transmission curve of a paint, in which a transmission zone, e.g., 1 to 7 µm, was measured to define key transmission "windows" for transmission imaging. Significantly progressive results were achieved to obtain data necessary to design the experiments for detecting corrosion and cracks in metal surfaces beneath a layer of paint using mid-infrared light.

In the experiment, the samples used were made from grade 2024 T3 aluminum plates, which were chemically corroded by the reaction of potassium hydroxide with the surface of the aluminum plate for a period of 24 hours. The thickness of the corrosion was about 35 µm and formed an 8 mm circle. The corrosion was either over coated with paint or covered with glass slides that had been prepared with different paints of various thickness. The over coated glass slides were prepared to measure absorption/transmission characteristics of the individual paints. Different commercial and military paints were studied.

The transmission curve of the paint illustrated in FIG. 1 indicates that paint has two transmittance zones for the wavelengths from 1 µm to 2.8 µm and from 3.8 µm to 5.5 µm. Military paint is comprised of a polyurethane primer layer, Strontium Chromate-TT-P-2760 Type 1 Class C, and a polyurethane topcoat, Mil-PRF-85285 Type 1 color 36173 gray. Absorption and scattering are the dominant mechanisms for the results displayed in FIG. 1. When an incident power on the sample at a particular wavelength is large enough, i.e., has a high enough signal to noise (S/N) ratio), imaging through an absorption layer is possible. The problem of imaging through paint layer is more complicated because of high scattering.

Figure 2:
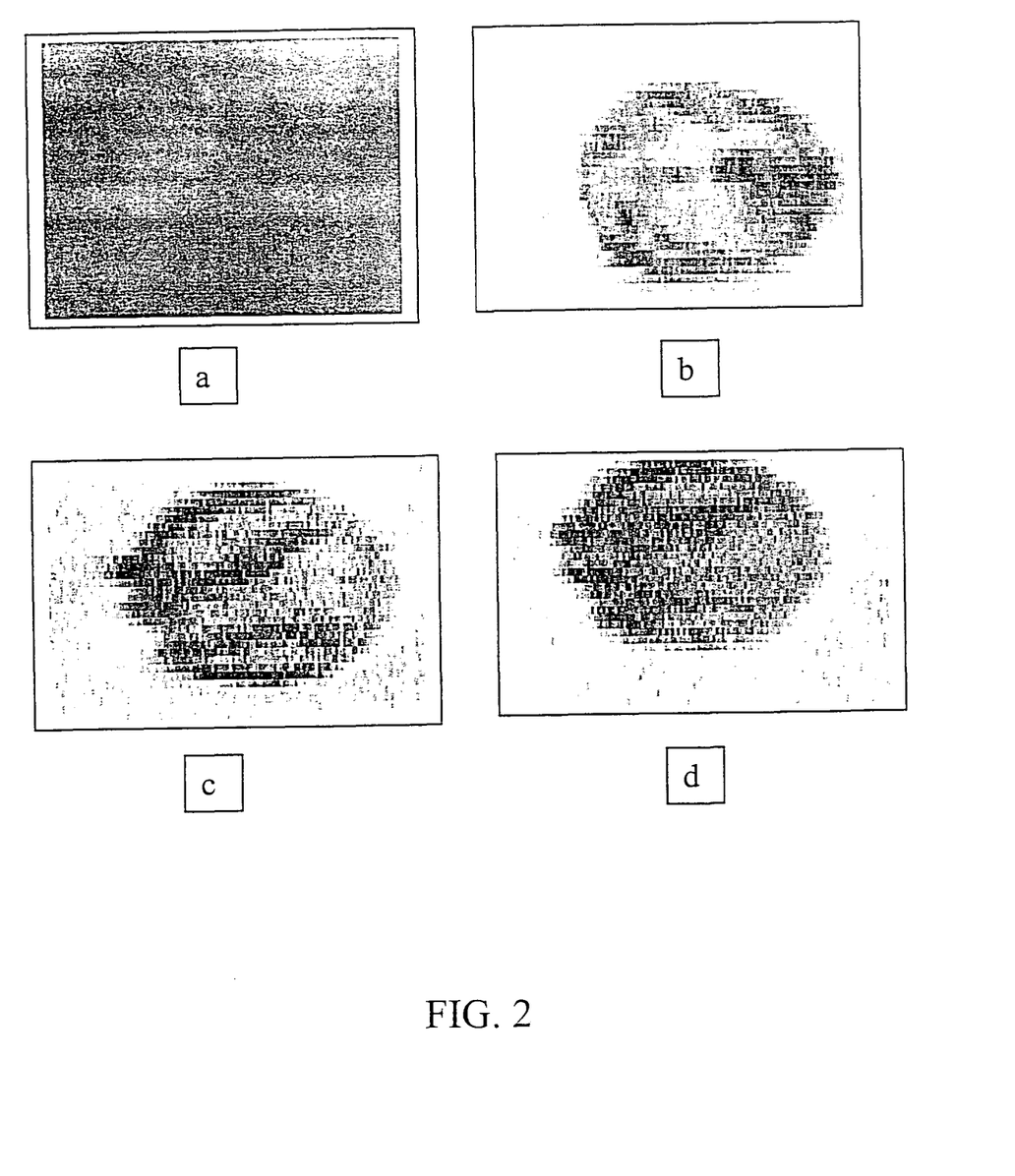
FIG. 2 illustrates images of corrosion on an aluminum plate using an MIR technique.

FIG. 2 illustrates images recorded at different MIR wavelengths. Specifically, FIG. 2 illustrates images at 1.8 µm, 3.8 µm, 4.8 µm, and 5.5 µm wavelengths, of corrosion over coated with a paint (0.004" thick). Image (a) is for the 1.8 µm wavelength (an NIR wavelength). Consequently, the corrosion region could not be imaged using NIR, because at this wavelength the transmission of the light is minimum and scattering is maximum compared to the other wavelengths. As the wavelength increases from 1.8 µm wavelength to the 3.8 µm wavelength (Image (b)) the transmission of light through the paint is higher and more photons reach the corrosion surface. The image for MIR of Image (c) (at 4.8 µm wavelength) has the best contrast, which correlates with the transmission curve of the paint. The optical transmission at the 5.5 µm wavelength is less then at the 4.8 µm wavelength. Accordingly, this results in the slightly poorer image as illustrated in Image (d).

The present invention provides a novel and useful optical system for scanning and detecting material abnormalities, e.g., cracks and corrosion, beneath a paint layer of an object such as an aircraft, a boat, a car, a bridge, etc. using a NIR and mid-infrared (MIR) light source with a wavelength range from 0.7 µm to 5.5 µm, as illustrated in FIGS. 1 and 2.

In the present invention, the size of cracks may vary from 5 µm to 20 µm, which defines the requirement resolution of the imaging objective and the CCD pixel size. The diffraction-limited diameter d of the beam spot d can be defined as $$d=f\cdot\theta \quad (1),$$

where $\theta$ is the full angle beam divergence, f is the focal length of the imaging objective.

$\theta$ can be calculated as $$\theta=2.4\lambda/d_o, \quad (2),$$

where do is the objective diameter.

For typical wavelength of $\lambda=5$ µm, $d_o=30$ mm and size of crack d=5 µm the objective focal length f is equal $$f=d/\theta=dd_o/2.4\lambda=10^{-2}\times30/2.4\times5\times10^{-3}\sim13 \; (mm). \quad (3).$$

With magnification 1 to 1 and a charge-coupled device (CCD) pixel size equal 24 um the crack resolution is equal about 25 µm. To resolve 5 µm cracks the objective magnification must be equal 5 to 1. The field of view is equal FOV=Nxp/M. When N=500 pixels, M=5 and p=24 um than FOV=500×0.024/5=2.4 mm.

Figure 3:
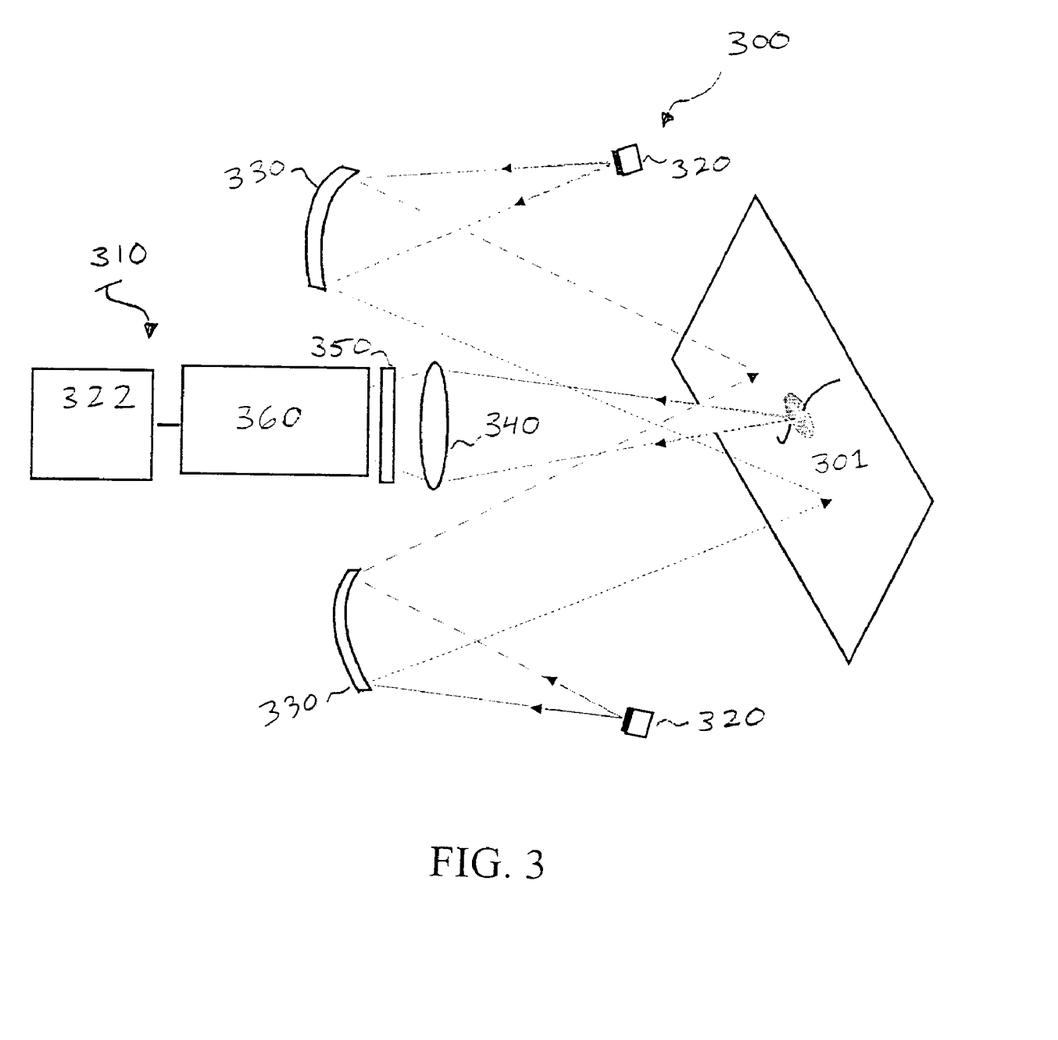
FIG. 3 is a diagram illustrating a detection system according to a first preferred embodiment of the present invention.

FIG. 3 is a diagram illustrating a MIR detection system according to a first preferred embodiment of the present invention. The system is usable in two-dimensional imaging of cracks and corrosion located under the paint of an object 301. As illustrated in FIG. 3, the system comprises a MIR illumination unit 300, which includes a source of MIR light 320, e.g., a halogen lamp, and directing parabolic mirrors 330, which direct the MIR on the object 301 that has a crack or corrosion beneath the paint layer. The system also comprises an MIR optical 2-D imaging system 310, which includes an MIR objective lens 340, a MIR narrow band filter 350, an MIR digital camera 360, e.g., a CCD or CMOS (complementary metal-oxide semiconductor) camera, and a display (or monitor) 322, for imaging the illuminated area of the coated surface.

In operation, the light emitted from the halogen lamps 320 is focused and reflected by the parabolic mirrors 330 onto the paint layer of object 301, which has a material abnormality, such as cracks or corrosion beneath it. The MIR objective lens 340 provides and focuses the cracks or corrosion to the MIR CCD camera 360, which is sensitive in the appropriate wavelength range. The MIR narrowband filter 350 is used to select the desirable spectral range of the illumination and the detected light. The image captured by the CCD camera 360 can then be displayed on the monitor 322.

Although the MIR light source is illustrated in FIG. 3 as a halogen lamp, other MIR sources such as a light emitting diode (LED) or IR laser diode could also be used.

Herein below, a number of alternate embodiments will be described in detail. However, because many of the components are the same as in FIG. 3 and perform in the same manner, descriptions of which have already been given above, only new components will be described below.

Figure 4:
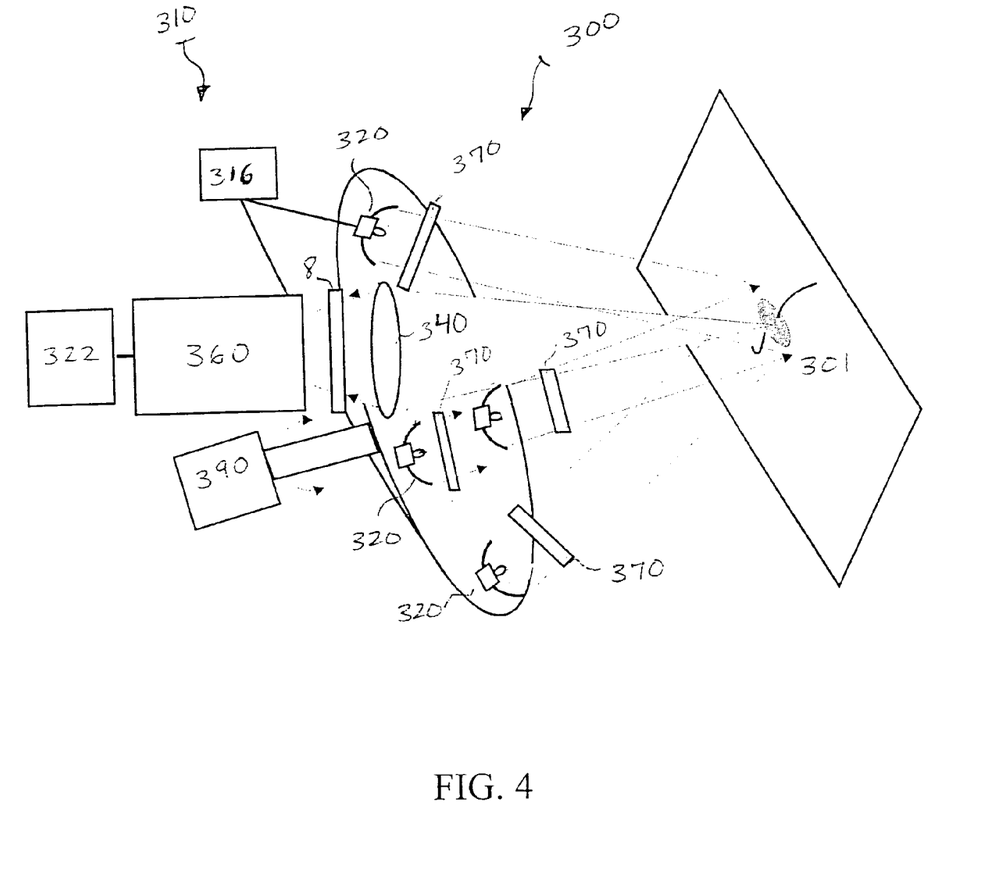
FIG. 4 is a diagram illustrating a detection system according to a second preferred embodiment of the present invention.

FIG. 4 is a diagram illustrating a detection system according to a second preferred embodiment of the present invention. More specifically, FIG. 4 illustrates an alternate embodiment of the system illustrated in FIG. 3. In FIG. 4, the MIR illumination unit 300 is comprised of a ring of MIR light sources 320 (with a power supply 316) and reflectors 303 with a common illuminating area placed on an object 301 and axes of rotation/dithering directed to the center of common illuminating area.

In addition, the system illustrated in FIG. 4 includes a motor 309 to rotate/dither the light sources 320. Polarizers 370 placed in the illuminating light beam pathway yield linearly polarized illumination light. A polarizer 8 is positioned in front of the CCD camera 360 for selection of the direction of detection polarization with an angle of rotation from 0 up to 90 degree, and its polarization oriented parallel or perpendicular to that of the polarizers 7 orientation.

Figure 5:
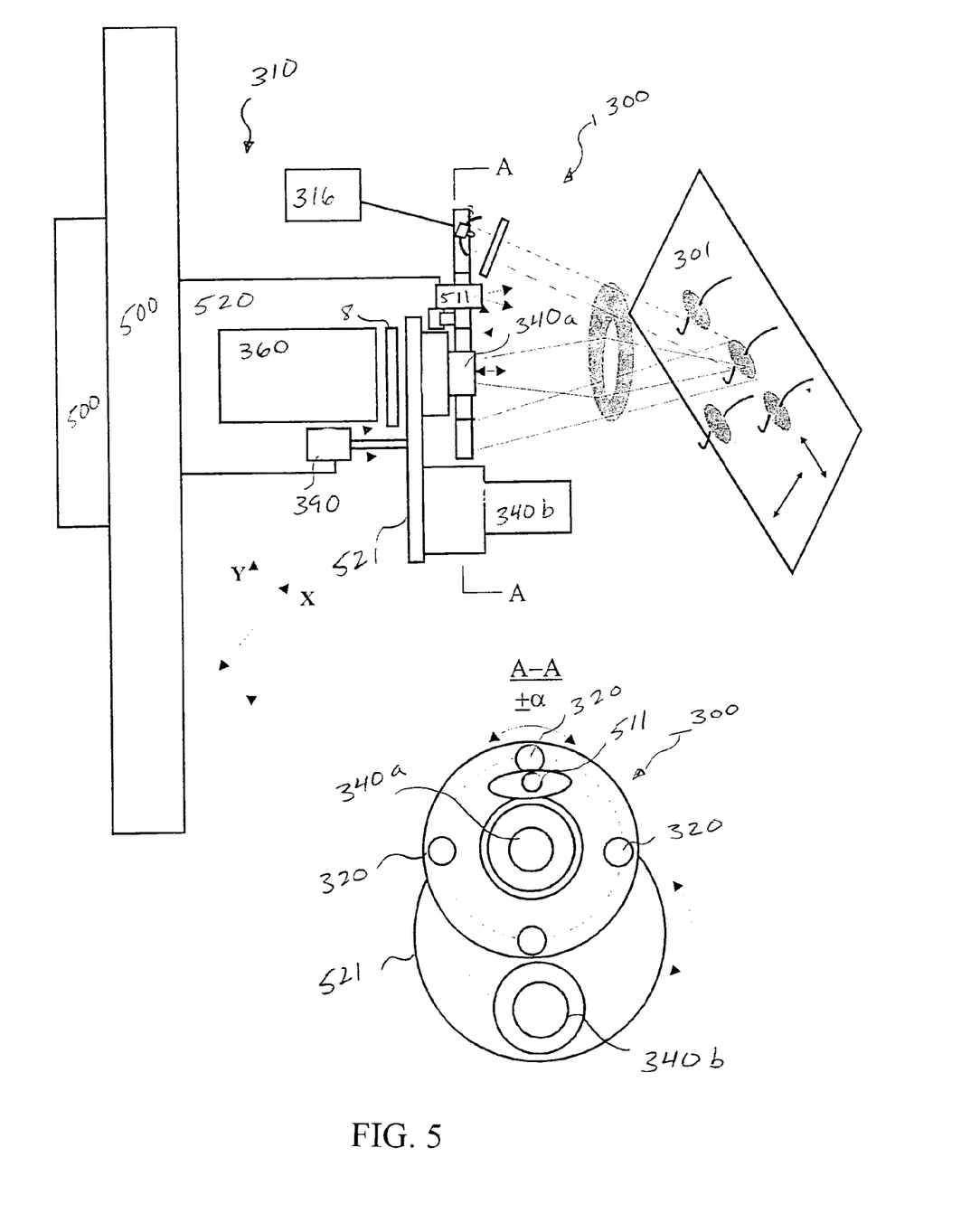
FIG. 5 is a diagram illustrating a detection system according to a third preferred embodiment of the present invention.

FIG. 5 is a diagram illustrating a detection system according to a third preferred embodiment of the present invention. Specifically, FIG. 5 illustrates an alternate embodiment of the system illustrated in FIG. 4.

In order to increase the imaging area of the optical system of FIG. 4, the system in FIG. 5 includes an X-Y scanning system 500, which may comprise sliding stages, to move the illumination unit 300 and the 2-D imaging system 310 relative to the object 301. The X-Y scanning system 500 includes a holder 520 to support the illumination unit 300 and the 2-D imaging system 310. The system also includes few MIR variable objective lenses 340a and 340b. Objective lenses are placed on a motorized platform 521 that can be remote rotated to place one of the objective lenses on the optical axis of the CCD camera 360. While the present embodiment is illustrated with two variable lenses, it should be appreciated by those skilled in the art that a similar system could be designed with more than two variable lenses. A range detector 511 with a feedback system connected to an objective zoom mechanism (not shown) is also provided to change the objective focal distance from the object 301.

Figure 6:
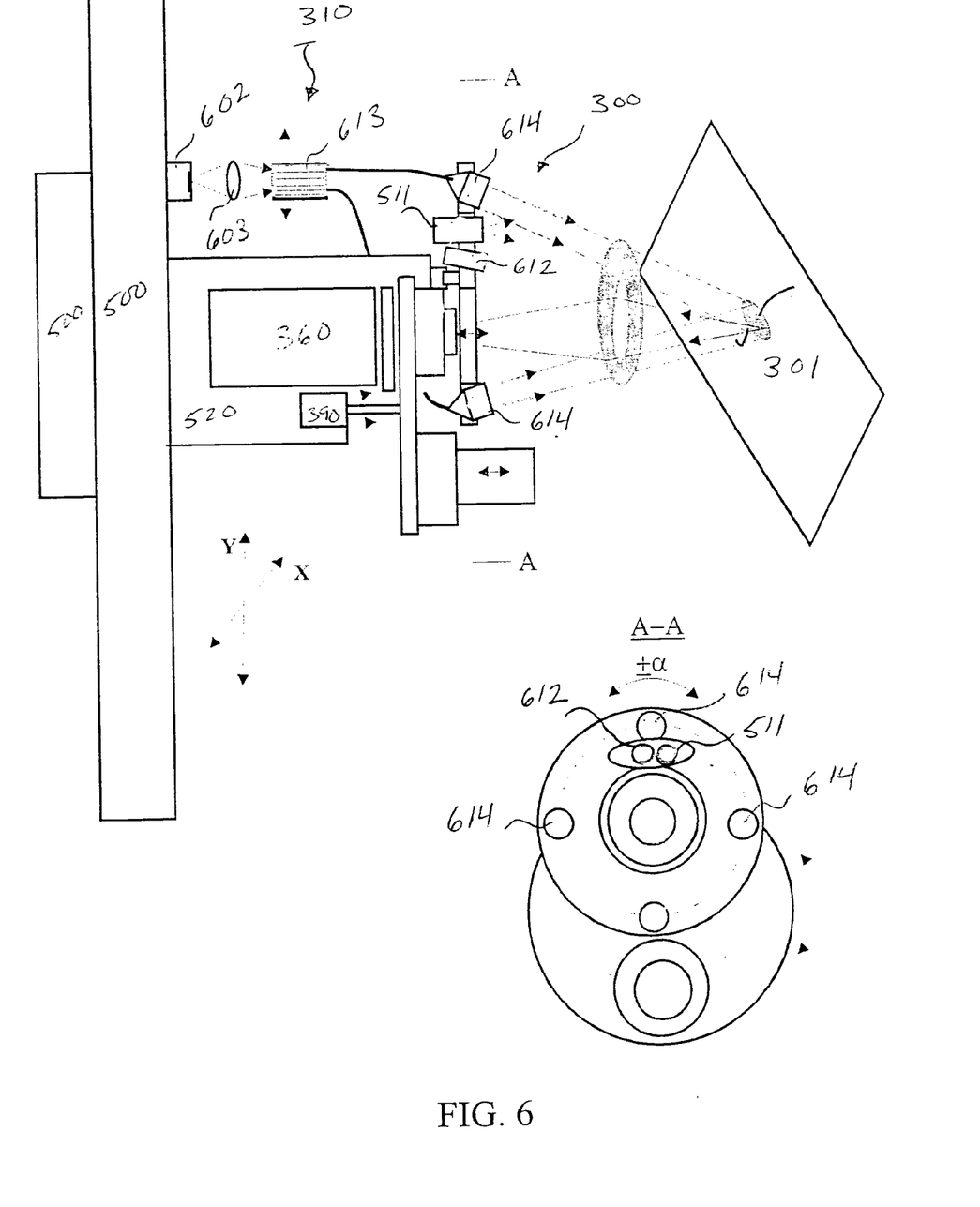
FIG. 6 is a diagram illustrating a detection system according to a fourth preferred embodiment of the present invention.

FIG. 6 is a diagram illustrating a detection system according to a fourth preferred embodiment of the present invention. Specifically, FIG. 6 illustrates an alternate embodiment of the system illustrated in FIG. 5. In FIG. 6, the illumination unit 310 comprises a fiber optic bundle 613 suitable for a wavelength range from 0.7 µm to 5.5 µm such as a bundle of hollow fibers and a ring of MIR lenses 614 with a common illuminating area placed on an object 301 and an axes of rotation/dithering directed to the center of common illuminating area. A MIR lens 603 is used to deliver a light from a MIR laser 602, e.g., a quantum cascade laser, to the fiber optic bundle 613. Additionally, a visible CCD camera 612 is used to image an illuminating area using visible light to monitor and control a surface of the sample.

Figure 7:
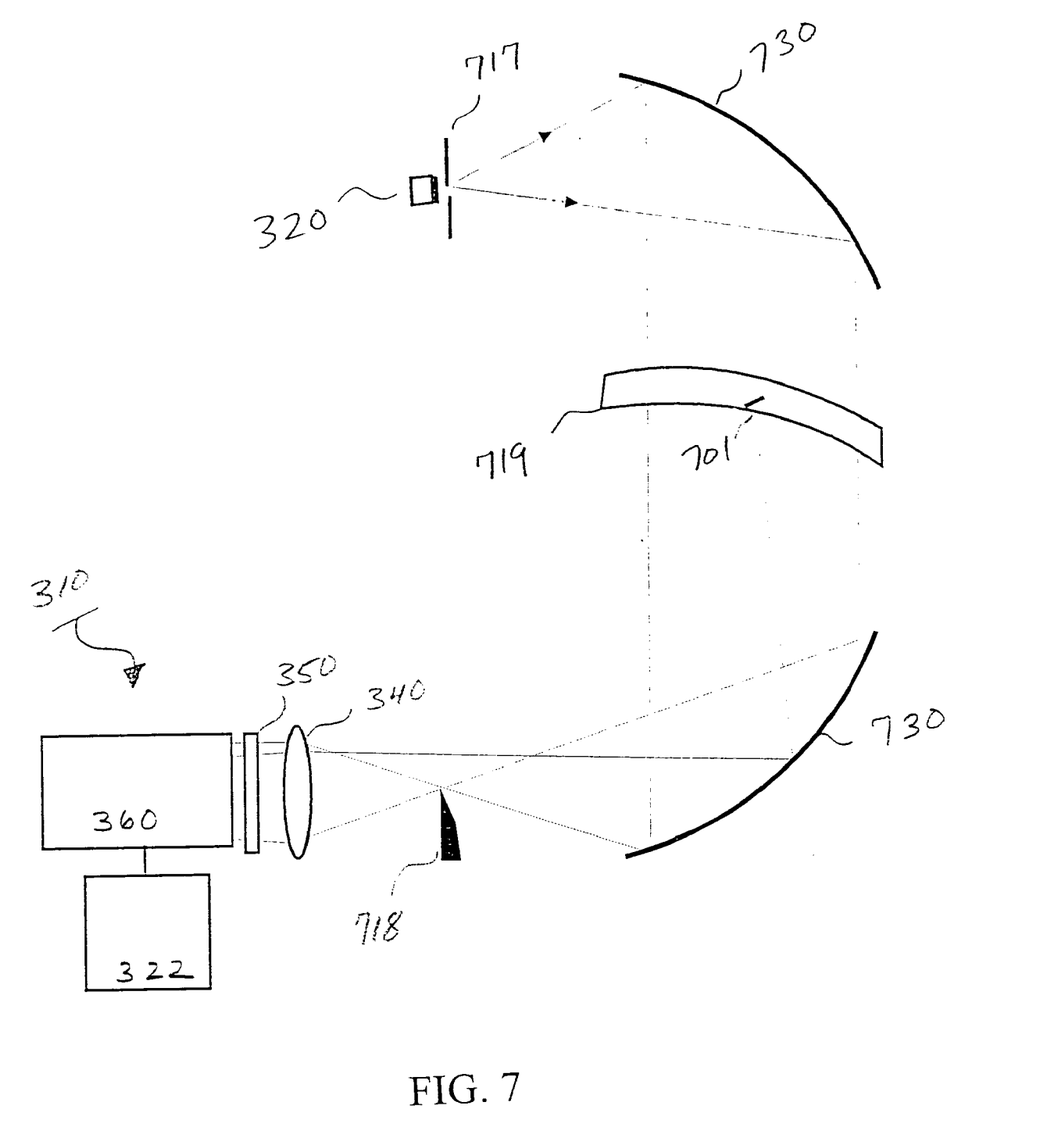
FIG. 7 is a diagram illustrating a detection system according to a fifth preferred embodiment of the present invention.

FIG. 7 is a diagram illustrating a detection system according to a fifth preferred embodiment of the present invention. In FIG. 7, in order to increase the sensitivity of the crack detection in accordance with the present invention, a slit 717 is placed in the focal plane of a parabolic mirror 703. A collimated beam is transmitted through an object 719, including of a crack 701. A second parabolic mirror 730 is provided to focus a beam into the focal plane consisting of a "knife" edge 718. Elements 717 and 718 and the two parabolic mirrors 703 and 730 produce a "slit-knife" shadow system. In this embodiment, for objects without cracks and scratches, a field of view is uniformly dark or gray. At the crack or scratch 701 the direction of the optical rays is scattered, producing a bright spot from the cracks 701. This signal can be recorded by the imaging system 310 producing significant sensitivity to the cracks 701 in the 2D image displayed on the monitor 322.

Figure 8:
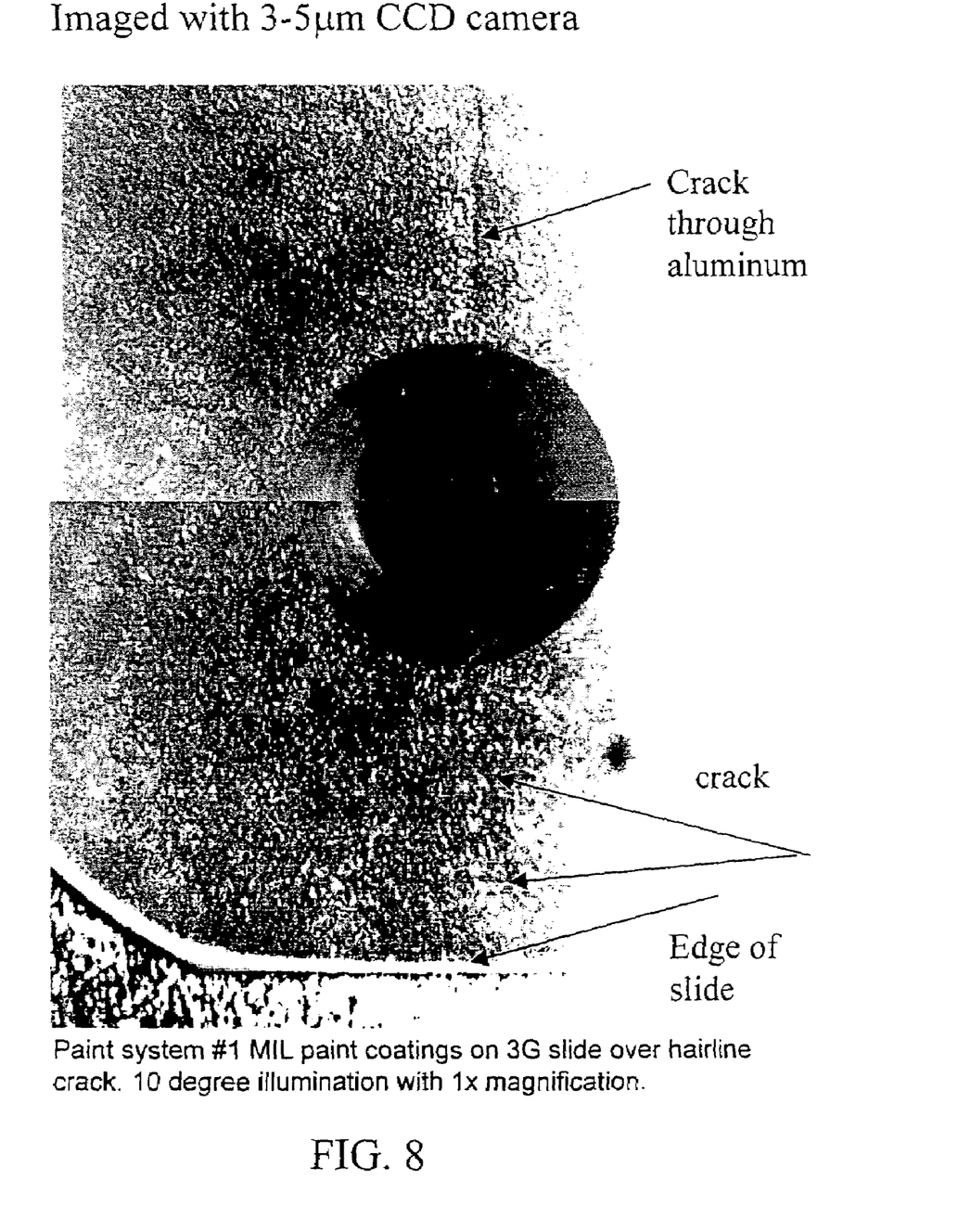
FIG. 8 illustrates an image of a crack in aluminum under a thick paint layer that was recorded utilizing an MIR CCD camera sensitive at 3 to 5 µm wavelengths, according to the present invention.

FIG. 8 illustrates an image of a crack in aluminum under a thick paint layer that was recorded utilizing a CCD camera sensitive at 3 to 5 µm wavelengths, according to the present invention. A crack on an aluminum plate under the paint system of 0.027" thickness is imaged using 14 bits MIR CCD camera sensitive in the wavelength range of 3 to 5 µm (with an InSb chip). As is illustrated in FIG. 8 and as described above, the present invention provides systems and methods for non-destructively detecting material abnormalities beneath a coated surface, in which a mid-infrared (MIR) illumination unit illuminates an area of the coated surface and a MIR 2-D imaging system, which includes an MIR CCD camera, captures an image of the illuminated area, thereby making it possible to detect an abnormality such as a crack beneath the coated surface.

While the invention has been shown and described with reference to certain preferred embodiments thereof, it will be understood by those skilled in the art that various changes in form and details may be made therein without departing from the spirit and scope of the invention as defined by the appended claims.

What is claimed is:

1. A system for non-destructively detecting material abnormalities beneath a coated surface, comprising:
   a mid-infrared (MIR) illumination unit for illuminating an area of the coated surface, the MIR illumination unit including at least one MIR light source, at least one polarizer located in front of the at least one MIR light source for providing linearly polarized light, and at least one reflector for reflecting and concentrating the polarized light from the light source on the illuminated area of the coated surface; and
   an MIR optical 2-D imager for imaging the illuminated area of the coated surface.

2. The system as recited in claim 1, wherein the MIR light source is at least one of a halogen lamp, a light emitting diode (LED), and a laser.

3. The system as recited in claim 1, wherein the at least one reflector is a parabolic mirror.

4. The system as recited in claim 1, wherein the at least one MIR light source and the at least one reflector are positioned in a ring around the optical 2-D imager having a common illuminating area on the coated surface and axes of rotation and dithering directed to a center of common illuminating area.

5. The system as recited in claim 1, wherein the MIR optical 2-D imager comprises:
   an MIR digital camera for capturing an image of a material abnormality under the illuminated area of the coated surface; and
   a display for displaying the image.

6. The system as recited as claim 5, wherein the MIR digital camera comprises one of an MIR charge-coupled device (CCD) camera and a complementary metal-oxide semiconductor (CMOS) camera.

7. The system as recited in claim 5, wherein the MIR 2-D optical imager further comprises at least one objective lens for focusing upon the illuminated area and providing the image to the MIR digital camera.

8. The system as recited in claim 7, wherein the MIR 2-D optical imager further comprises a motorized platform for rotating the at least one objective lens about the illuminated area.

9. The system as recited in claim 7, wherein the MIR 2-D optical imager further comprises:
   a range detector for determining a distance between the at least one objective lens and the coated surface; and
   a zoom mechanism for adjusting an objective focal distance from the coated surface.

10. The system as recited in claim 1, wherein the MIR illumination unit comprises:
    an MIR laser for providing MIR light;
    at least one fiber optic cable; and
    at least one MIR lens for projecting the MIR light from the MIR laser, which is transmitted through the at least one fiber optic cable to the at least one MIR lens, on the illuminated area of the coated surface.

11. The system as recited in claim 1, further comprising at least one stage for moving the system in at least one of X and Y directions.

12. The system as recited in claim 1, wherein the MIR light source and the MIR optical 2-D imager have a wavelength range from 2 µm to 5.5 µm.

13. The system as recited in claim 1, wherein the surface is metal.

14. The system as recited in claim 1, wherein the coating is paint.

15. The system as recited in claim 1, wherein the material abnormalities include at least one of deterioration, corrosion, and cracking.

16. A method for non-destructively detecting material abnormalities beneath a coated surface, comprising the steps of:
    illuminating an area of the coated surface by a mid-infrared (MIR) light source having at least one polarizer located in front of the MIR light source for providing linearly polarized light; and
    imaging the surface below the illuminated area of the coated surface with an MIR optical 2-D imager.

17. The method as recited in claim 16, further comprising displaying the 2-D image on a display.

18. The method as recited in claim 16, further comprising imaging a next area of the coated surface.

19. The method as recited in claim 18, wherein the step of imaging the next area comprises moving the MIR light source and the MIR optical 2-D imager in at least one of X and Y directions.

20. The method as recited in claim 16, wherein the MIR light source and the MIR optical 2-D imager have a wavelength range from 2 µm to 5.5 µm.

21. The method as recited in claim 16, wherein the surface is metal.

22. The method as recited in claim 16, wherein the coating is paint.

23. The method as recited in claim 16, wherein the abnormalities include at least one of deterioration, corrosion, and cracking.

* * * * *